(12) United States Patent
Wakabayashi

(10) Patent No.: US 8,439,893 B2
(45) Date of Patent: May 14, 2013

(54) SYSTEM AND METHOD FOR EFFICIENT DRAINAGE OF BODY CAVITY

(75) Inventor: Akio Wakabayashi, Murrieta, CA (US)

(73) Assignee: Medela Holding AG, Baar (CH)

( * ) Notice: Subject to any disclaimer, the term of this patent is extended or adjusted under 35 U.S.C. 154(b) by 219 days.

(21) Appl. No.: 10/517,908

(22) PCT Filed: Jun. 11, 2003

(86) PCT No.: PCT/US03/18505
§ 371 (c)(1),
(2), (4) Date: Jan. 30, 2006

(87) PCT Pub. No.: WO03/103744
PCT Pub. Date: Dec. 18, 2003

(65) Prior Publication Data
US 2006/0122575 A1   Jun. 8, 2006

Related U.S. Application Data

(60) Provisional application No. 60/388,398, filed on Jun. 11, 2002.

(51) Int. Cl.
*A61M 27/00* (2006.01)
(52) U.S. Cl.
USPC .......................................................... 604/541
(58) Field of Classification Search ............... 604/19, 604/48, 93.01, 164.04, 264, 268, 314, 322, 604/540, 541, 35, 542; 600/571
See application file for complete search history.

(56) References Cited

U.S. PATENT DOCUMENTS 1,188,180 A * 6/1916 Kells ................................ 604/45
1,740,174 A * 12/1929 Hevern ........................ 27/24.1
(Continued)

FOREIGN PATENT DOCUMENTS

EP   0236853    9/1987
FR   2256769    8/1975
(Continued)

OTHER PUBLICATIONS

Wakabayashi, et al., *High Vacuum Drainage of the Chest Using a Miniature Double Lumen Chest Tube*. ASAIO Journal, 2003, pp. 300-303.

(Continued)

*Primary Examiner* — Kevin C Sirmons
*Assistant Examiner* — Michael J Anderson
(74) *Attorney, Agent, or Firm* — McDonnell Boehnen Hulbert & Berghoff LLP

(57) ABSTRACT

A system for efficient drainage of a body cavity includes application of vacuum at very high pressure, preferably in the range of approximately 50-500 torr or higher. The system includes the use of a drainage tube having a plurality of holes formed into the wall of a portion of the tube to be inserted in the body cavity. The area of each of the holes is preferably selected to ensure that the suction force communicated by each of the holes to areas within the body cavity is insufficient to injure the tissues exposed in the body cavity. A one-way valve maintains unidirectional flow of drained fluids and gases away from the body cavity. A vacuum relief valve prevents application of dangerous levels of vacuum pressure by opening to admit atmospheric air when vacuum pressure exceeds a predetermined threshold. A vacuum chamber separates drained fluids from drained gases.

5 Claims, 2 Drawing Sheets

U.S. PATENT DOCUMENTS

| | | | | |
|---|---|---|---|---|
| 2,614,563 | A * | 10/1952 | Devine, Jr. | 604/45 |
| 2,930,378 | A * | 3/1960 | Buyers | 604/45 |
| 3,142,298 | A * | 7/1964 | Koski et al. | 604/31 |
| 3,416,532 | A * | 12/1968 | Grossman | 604/267 |
| 3,421,510 | A * | 1/1969 | Kettenbach | 604/45 |
| 3,520,300 | A * | 7/1970 | Guiles, Jr | 604/269 |
| 3,528,427 | A * | 9/1970 | Sheridan et al. | 604/45 |
| 3,628,532 | A | 12/1971 | Magrath | |
| 3,680,562 | A * | 8/1972 | Wittes et al. | 604/500 |
| 3,683,913 | A | 8/1972 | Kurtz et al. | |
| 3,809,085 | A | 5/1974 | Bidwell et al. | |
| 3,810,471 | A * | 5/1974 | Truhan | 604/45 |
| 3,830,238 | A | 8/1974 | Kurtz et al. | |
| 3,908,664 | A * | 9/1975 | Loseff | 604/98.02 |
| 3,945,385 | A | 3/1976 | Sackner | |
| 3,993,080 | A * | 11/1976 | Loseff | 604/28 |
| 4,015,603 | A | 4/1977 | Kurtz et al. | |
| 4,018,224 | A | 4/1977 | Kurtz et al. | |
| 4,068,664 | A * | 1/1978 | Sharp et al. | 604/268 |
| D248,969 | S * | 8/1978 | Hodge | D24/112 |
| 4,105,031 | A | 8/1978 | Kurtz et al. | |
| 4,112,947 | A * | 9/1978 | Nehring | 604/30 |
| 4,112,948 | A | 9/1978 | Kurtz et al. | |
| 4,137,940 | A | 2/1979 | Faisandier | |
| 4,180,074 | A * | 12/1979 | Murry et al. | 604/31 |
| 4,182,343 | A * | 1/1980 | Inaba | 604/268 |
| 4,182,385 | A * | 1/1980 | Williamson | 141/65 |
| 4,291,276 | A | 9/1981 | Ida | |
| 4,291,694 | A * | 9/1981 | Chai | 604/512 |
| 4,299,222 | A | 11/1981 | Eckenhoff | |
| 4,317,452 | A * | 3/1982 | Russo et al. | 604/541 |
| 4,382,442 | A * | 5/1983 | Jones | 604/28 |
| 4,391,276 | A | 7/1983 | Lazarus et al. | |
| 4,398,910 | A * | 8/1983 | Blake et al. | 604/266 |
| 4,421,505 | A * | 12/1983 | Schwartz | 604/28 |
| 4,451,257 | A * | 5/1984 | Atchley | 604/119 |
| 4,508,533 | A * | 4/1985 | Abramson | 604/35 |
| 4,573,965 | A * | 3/1986 | Russo | 604/30 |
| 4,650,463 | A | 3/1987 | LeVeen et al. | |
| 4,692,153 | A * | 9/1987 | Berlin et al. | 604/171 |
| 4,710,165 | A * | 12/1987 | McNeil et al. | 604/67 |
| 4,735,606 | A * | 4/1988 | Davison | 604/28 |
| 4,756,501 | A | 7/1988 | Quercia et al. | |
| 4,781,678 | A * | 11/1988 | de Couet et al. | 604/45 |
| 4,784,638 | A * | 11/1988 | Ghajar et al. | 604/523 |
| 4,784,642 | A | 11/1988 | Everett, Jr. et al. | |
| 4,820,284 | A * | 4/1989 | Hauri | 604/318 |
| D303,840 | S * | 10/1989 | Weilbacher | D24/112 |
| 4,883,474 | A | 11/1989 | Sheridan et al. | |
| 4,917,667 | A * | 4/1990 | Jackson | 604/103 |
| 4,923,451 | A | 5/1990 | McCormick | |
| 4,936,834 | A * | 6/1990 | Beck et al. | 604/264 |
| 4,941,469 | A | 7/1990 | Adahan | |
| 4,955,873 | A | 9/1990 | Rajlevsky | |
| 4,955,874 | A | 9/1990 | Farrar et al. | |
| 5,002,054 | A * | 3/1991 | Ash et al. | 600/347 |
| 5,044,362 | A | 9/1991 | Younes | |
| 5,045,075 | A | 9/1991 | Ersek | |
| 5,083,572 | A * | 1/1992 | Pokorny | 600/581 |
| 5,100,395 | A * | 3/1992 | Rosenberg | 604/284 |
| 5,108,364 | A * | 4/1992 | Takezawa et al. | 604/43 |
| 5,141,503 | A * | 8/1992 | Sewell, Jr. | 604/317 |
| 5,149,325 | A * | 9/1992 | Telang et al. | 604/119 |
| 5,186,714 | A * | 2/1993 | Boudreault et al. | 604/21 |
| 5,203,769 | A * | 4/1993 | Clement et al. | 604/32 |
| 5,211,171 | A | 5/1993 | Choromokos | |
| 5,221,255 | A * | 6/1993 | Mahurkar et al. | 604/43 |
| 5,223,228 | A * | 6/1993 | Telang et al. | 422/104 |
| 5,300,050 | A | 4/1994 | Everett, Jr. et al. | |
| 5,318,510 | A | 6/1994 | Cathcart | |
| 5,360,414 | A * | 11/1994 | Yarger | 604/264 |
| 5,370,610 | A * | 12/1994 | Reynolds | 604/43 |
| 5,380,245 | A * | 1/1995 | Reiterman et al. | 454/63 |
| 5,417,664 | A * | 5/1995 | Felix et al. | 604/129 |
| 5,419,768 | A * | 5/1995 | Kayser | 604/119 |
| 5,423,780 | A * | 6/1995 | Malette | 604/317 |
| 5,429,601 | A * | 7/1995 | Conley et al. | 604/65 |
| 5,458,567 | A | 10/1995 | Cathcart | |
| 5,484,399 | A * | 1/1996 | DiResta et al. | 604/21 |
| 5,484,401 | A * | 1/1996 | Rodriguez et al. | 604/28 |
| 5,507,734 | A | 4/1996 | Everett, Jr. et al. | |
| 5,527,276 | A * | 6/1996 | Bruce | 604/506 |
| 5,578,006 | A | 11/1996 | Schön | |
| 5,588,167 | A | 12/1996 | Pahno et al. | |
| 5,738,656 | A * | 4/1998 | Wagner | 604/119 |
| 5,800,408 | A * | 9/1998 | Strauss et al. | 604/264 |
| 5,807,313 | A | 9/1998 | Deik et al. | |
| 5,980,483 | A * | 11/1999 | Dimitri | 604/102.01 |
| 6,017,493 | A * | 1/2000 | Cambron et al. | 422/44 |
| 6,024,731 | A * | 2/2000 | Seddon et al. | 604/317 |
| 6,299,593 | B1 * | 10/2001 | Wakabayashi | 604/48 |
| 6,352,525 | B1 * | 3/2002 | Wakabayashi | 604/322 |
| 6,478,789 | B1 | 11/2002 | Spehalski et al. | |
| 6,543,452 | B1 * | 4/2003 | Lavigne | 128/207.18 |
| 6,620,132 | B1 * | 9/2003 | Skow | 604/131 |
| 6,626,891 | B2 * | 9/2003 | Ohmstede | 604/543 |
| 6,638,253 | B2 * | 10/2003 | Breznock | 604/164.04 |
| 6,641,575 | B1 * | 11/2003 | Lonky | 604/540 |
| 6,648,862 | B2 * | 11/2003 | Watson | 604/319 |
| 6,849,061 | B2 * | 2/2005 | Wagner | 604/99.02 |
| 6,878,142 | B2 * | 4/2005 | Lawrence et al. | 604/540 |
| 6,893,425 | B2 | 5/2005 | Dunn et al. | |
| 6,979,324 | B2 * | 12/2005 | Bybordi et al. | 604/313 |
| 6,989,016 | B2 * | 1/2006 | Tallarida et al. | 606/142 |
| 7,013,890 | B2 | 3/2006 | Wakabayshi | |
| 7,090,663 | B2 | 8/2006 | Dunn et al. | |
| 7,125,402 | B1 | 10/2006 | Yarger | |
| 7,141,045 | B2 * | 11/2006 | Johansson et al. | 604/508 |
| 7,198,751 | B2 * | 4/2007 | Carpenter et al. | 422/45 |
| 7,201,870 | B2 * | 4/2007 | Olsen et al. | 422/44 |
| 7,204,958 | B2 * | 4/2007 | Olsen et al. | 422/44 |
| 7,214,202 | B1 * | 5/2007 | Vogel et al. | 601/11 |
| 7,335,334 | B2 * | 2/2008 | Olsen et al. | 422/45 |
| 7,338,482 | B2 * | 3/2008 | Lockwood et al. | 604/543 |
| 2001/0029956 | A1 * | 10/2001 | Argenta et al. | 128/897 |
| 2002/0058915 | A1 * | 5/2002 | Wakabayashi | 604/319 |
| 2002/0082587 | A1 * | 6/2002 | Noda | 604/544 |
| 2002/0161346 | A1 * | 10/2002 | Lockwood et al. | 604/315 |
| 2002/0193761 | A1 * | 12/2002 | Lord | 604/323 |
| 2003/0149407 | A1 | 8/2003 | Diresta et al. | |
| 2004/0073154 | A1 * | 4/2004 | Borgesen | 604/8 |
| 2006/0015087 | A1 * | 1/2006 | Risk et al. | 604/541 |
| 2006/0122575 | A1 * | 6/2006 | Wakabayashi | 604/541 |
| 2006/0259014 | A1 | 11/2006 | Yarger | |
| 2007/0135795 | A1 * | 6/2007 | De Paulis | 604/541 |

FOREIGN PATENT DOCUMENTS

| | | |
|---|---|---|
| FR | 2724113 | 3/1996 |
| GB | 1458483 | 12/1976 |
| JP | 51-66183 | 6/1976 |
| WO | 03/103744 | 12/2003 |

OTHER PUBLICATIONS

Shackcloth, et al., "Management of Sternal Would Complications by High-Pressure Suction Drainage via a Polyurethane Foam," Ann. Thorac. Surg., 2001; 72:976-984.

Grobmyer et al., "High-Pressure Gradients Generated by Closed-Suction Surgical Drainage Systems," Surgical Infections, vol. 3, No. 3, 2002, pp. 245-249.

Catarino et al., "High-Pressure Suction Drainage via a Polyurethane Foam in the Management of Poststernotomy Mediastintis," Ann. Thorac Surg., 2000; 70:1891-1895.

Sagar et al., "Randomized trial of drainage of colorectal anastomosis," Br. J. Surg., 1993, vol. 80, Jun., 769-771.

Aldo da Cunha Medeiros, MD et al., "Treatment of Enterocutaneous Fistulas by High-Pressure Suction with a Normal Diet," The American Journal of Surgery, vol. 159, pp. 411-413 (Apr. 1990).

Smith, S R G et al., "Surgical drainage," British Journal of Hospital Medicine, pp. 308, 311, 314-315 (Jun. 1985).

Moriwaki et al., "Usefulness of High Pressure Aspiration with Overcoated Double Luminal Draining Tube to Prevent of Abdominal Sepsis (Abscess and Anastomotic Leakage)," Jpn J Gastroetnerol Surg, 35:473-479 (2002) Abstract.

Kadohama et al., "Vacuum-assisted Would Closure in the Management of Deep Sternal Wound Infection," Japanese Journal of Thoracic Surgery, vol. 60, No. 12, pp. 1066-1068 (Abstract) 2007.

Wedderburn et al., "Comparison between low and high pressure suction drainage following axillary clearance," European Journal of Surgical Oncology, 2000; 26:142-144.

Salam et al., "A comparison of two types of vacuum drainage after cholecystectomy," Annals of the Royal College of Surgeons of England (1984), vol. 66, pp. 190-191.

Britton et al., "A comparison between disposable and non-disposable suction drainage units: a report of a controlled trial," Br. J. Surg., vol. 66 (1979), pp. 279-280.

Kuroi et al., "Evidence-Based Risk Factors for Seroma Formation in Breast Surgery," Jpn J. Clin Oncol., 2006; 36 (4):197-206.

Van Heurn et al., "Prospective randomized trial of high versus low vacuum drainage after axillary lymphadenectomy," Br. Journal of Surgery, 1995, 82, 931-932.

Bonnema MD, Jorien et al., "A Prospective Randomized Trial of High Versus Low Vacuum Drainage after Axillary Dissection for Breast Cancer," The American Journal of Surgery, vol. 173, pp. 76-79 (Feb. 1997).

Chintamani et al., "Half versus full vacuum suction drainage after modified radical mastectomy for breast cancer—a prospective randomized clinical trial [ISRCTN24484328]," BMC Cancer 2005, 5:11 (Jan. 27, 2005).

Bar-El et al., "Potentially Dangerous Negative Intrapleural Pressures Generated by Ordinary Pleural Drainage Systems," Chest, 2001; 119:511-514.

Miller, K.S. et al., "Chest Tubes, Indications, Technique, Management and Complications," Chest, 1987, 91:358-264.

Burgos, Raul et al., "Pulmonary Hydaitosis: Surgical Treatment and Follow-Up of 240 Cases," European Journal of Cardio-thoracic Surgery, 16 (1999) 628-635.

Rescigno et al., "Continuous High Vacuum and Primary Skin Closure in Sternotomy Wound Infection," European Journal of Cardio-thoracic Surgery, 19 (2001) 375.

Gwozdziewicz MD., Marek et al., "An alternative Approach for Chest Drainage after Cardiac Surgery: Redon Drains," The Journal of Thoracic and Cardiovascular Surgery (Jan. 2008) pp. 216-217.

Newcomb et al., "High-vacuum drains rival conventional underwater-seal drains after pediatric heart surgery," European Journal of Cardio-thoracic Surgery, 27 (2005) 395-400.

* cited by examiner

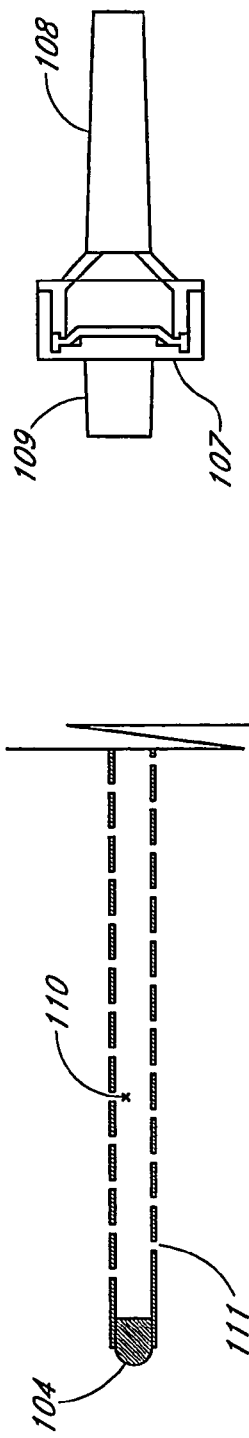
FIG. 1B
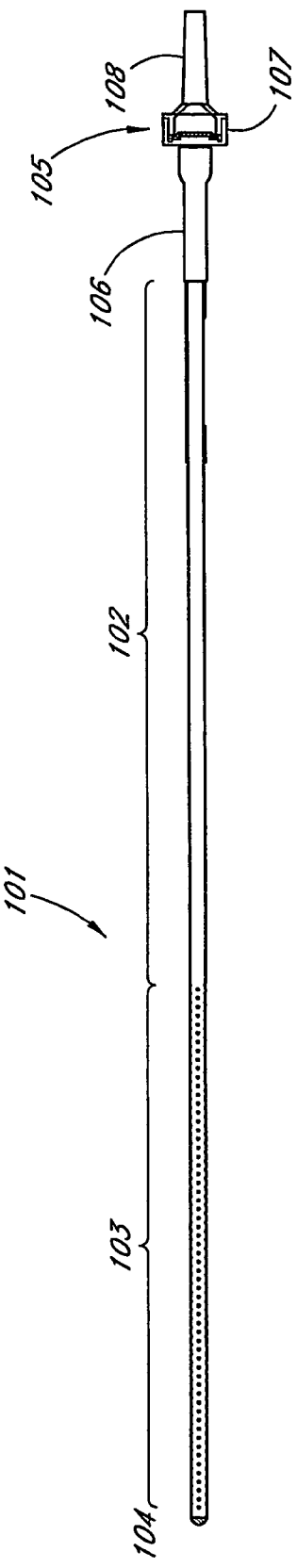
FIG. 1C
FIG. 1A

SYSTEM AND METHOD FOR EFFICIENT DRAINAGE OF BODY CAVITY

RELATED APPLICATION INFORMATION

This application is a national phase application under 35 U.S.C. §371 of International Patent Application No. PCT/US2003/018505, filed Jun. 11, 2003, and claims priority under 35 U.S.C. §119(e) to provisional application Ser. No. 60/388,398 filed Jun. 11, 2002.

BACKGROUND OF THE INVENTION

1. Field of the Invention

This invention relates to the field of drainage of gas and fluid from a body cavity, and, for example, applies to problems associated with draining a chest cavity.

2. Description of the Related Art

When a mammalian chest cavity contains gas and/or fluid, a lung cannot function normally. One way to relieve this problem is to evacuate the problematic gas and/or fluid by a drainage system. Also, in certain procedures such as, for example, open heart surgery, accumulating blood needs to be drained before it clots to avoid complications.

Body cavity drainage systems typically consist of a tubular structure, either round or square or any other shape, made of resilient polymer such as polyvinyl chloride, silicone rubber, polyurethane, etc. and other components including or directing a vacuum source. The vacuum source can be satisfied a number of ways, including a centrally installed vacuum line as found in the majority of medical facilities, a portable vacuum pump providing vacuum generated by an electrical motor and pump, or a self-expanding spring-loaded blood evacuation device. A portable vacuum pump may be configured in accordance with the Portable Modular Chest Drainage System of U.S. Pat. No. 6,352,525 B1.

Traditionally, according to well-known techniques, a flexible tube made of polymer is inserted into the body cavity and connected to a body drainage device to remove gas and/or fluid. Many different sizes of drainage tubes are available, including those ranging from 8 F to 41 F. Existing chest drainage devices are similar in design and typically include a fluid collection reservoir, a bubble chamber to indicate gas leaks from the chest cavity, and a water column to regulate vacuum pressure and prevent influx of atmospheric air in case vacuum pressure is lost from the drainage system. In some units, a water column is replaced with a pressure gauge.

Existing chest drainage systems conventionally use a low vacuum pressure. In such systems, the vacuum pressure applied to the chest tube is normally −20 cmH$_2$0 (=14.7 torr) or less. A dry unit with a pressure gauge may use higher pressure, but only slightly higher.

In order to function adequately at conventional vacuum pressure, a large chest tube is necessary. In most existing systems, in order to increase suction area of the tube, side holes, two to six in number, are created. A large chest tube will cause pain at the entry site, increase the chance of would infection and may compress the lung or heart. While a small bore tube may be better tolerated by a patient, a small bore tube may not function adequately at conventional vacuum pressure, and the widely recognized dangers associated with the use of higher vacuum pressures, including damage to body tissue, have discouraged the use of high vacuum pressure to activate small bore drainage tubes.

Thus, there is presently a need for a system and method for increasing drainage efficiency while avoiding the risk of damage to body tissue.

SUMMARY OF THE INVENTION

In one embodiment, the present invention includes apparatus and methods relating to one or a combination of basic principles: (1) very high vacuum pressure providing an overall drainage force substantially higher than that used with existing systems, (2) minimized suction force applied directly to body tissue, (3) a compact vacuum relief valve that may replace a bulky conventional chest drainage device, and/or (4) a one-way check valve. Generally, embodiments of the present invention include very high vacuum pressure and a small bore drainage tube with a plurality of small side holes. The small bore drainage tube may include or have a connector incorporating a one-way valve. Embodiments may also include a vacuum chamber which may use a vacuum relief valve.

In one embodiment, the present invention is a drainage tube having first and second ends. The drainage tube is constructed to receive around 50 torr or more of vacuum pressure at a first end. An insertion portion of the drainage tube near the second end has a plurality of small holes, the insertion portion adapted to be inserted into a mammalian body cavity. The quantity of small holes and area of each are selected to ensure that when the vacuum pressure is applied at the first end with the insertion portion of the drainage tube inserted into the body cavity, the suction force at each of the small holes is insufficient to cause injury to proximate body tissues. In a preferred embodiment, the drainage tube corresponds to sizes ranging from 4 F to 15 F (F will be understood to mean French). In another preferred embodiment, the area of each hole ranges from around that of a circle having a diameter of 0.5 mm to around that of a circle having a diameter of 1 mm. In yet another preferred embodiment, the drainage tube has a circular cross section. The drainage tube may be either single or double lumen.

In another embodiment, the present invention comprises a connector for a drainage tube that incorporates a one-way check valve. The one-way check valve may replace a bulky water seal of a conventional chest drainage system. The connector has inlet and outlet ends. The inlet end of the connector is coupled to the outlet end of the drainage tube. The connector includes a one-way valve, which may of a diaphragm type or another type. The one-way valve may be adapted to maintain unidirectional gas and/or fluid flow away from the body cavity. The one-way valve may also be adapted to prevent influx of atmospheric air into the body cavity if the drainage system loses vacuum pressure.

In another embodiment, the invention comprises a vacuum chamber having a vacuum relief valve of a diaphragm type, spring-coil type, or another type. The vacuum relief valve opens to direct influx of atmospheric air into the vacuum chamber to equalize the vacuum pressure to a predetermined level if excess vacuum pressure builds up. Inlet ports of the vacuum chamber may be connected to one to three drainage tubes using standard connecting tubing. A gas outlet port of the vacuum chamber is connected to a vacuum source, either a portable vacuum pump or central vacuum line of the medical facility via standard connector tubing. A fluid drainage outlet port of the vacuum chamber is connected to a rigid fluid reservoir or a standard blood collection bag with or without anti-coagulant. Additional exemplary embodiments of the present invention will be described in more detail below.

BRIEF DESCRIPTION OF THE DRAWINGS

FIG. 1A illustrates a perspective view of a drainage tube in accordance with one embodiment of the present invention;

FIG. 1B illustrates an enlarged, axial cross-sectional view near the tip of the drainage tube;

FIG. 1C illustrates an enlarged perspective view of a connector in accordance with an embodiment of the present invention.

DETAILED DESCRIPTION

Figure 2:
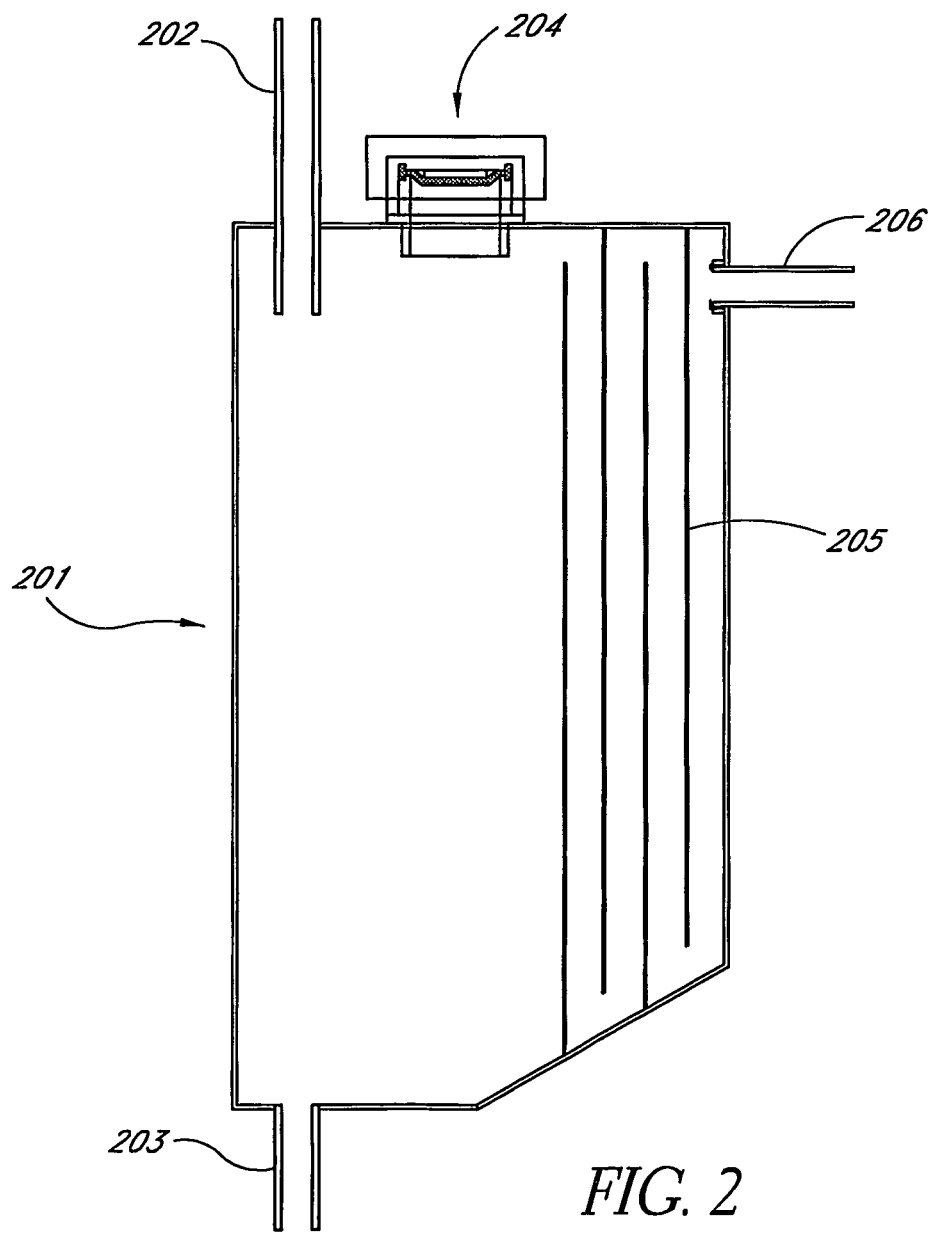
FIG. 2 illustrates a representation of a vacuum chamber in accordance with an embodiment of the present invention.

The design and operation of a gas/fluid drainage system is influenced by many factors, including efficiency and safety. The efficiency of a chest tube for removing gas is determined by total suction force, and the safety of the drainage is determined by the suction force applied to the body tissue through the largest opening of the drainage tube.

The total suction force is a product of total suction area times vacuum pressure. Total suction area is a sum of cross-sectional area of the open end of the tube and total opening areas of side holes. If the end of the tube is closed, the total suction area is a product of the opening area of a side hole times number of side holes. The number of side holes is limited by the length, diameter and wall thickness of the tube. Side holes are generally created only in the part of the tube that will stay inside the body cavity being drained. In this description, 15 cm is used as an example, though it will be appreciated that other lengths may be used. Also the diameter of each side hole cannot exceed a certain percentage of the circumference of the tube so that the tube will not lose structural strength.

Suction force applied to a tissue surrounding the drainage tube is a product of an opening area of the tube and vacuum pressure applied to the drainage tube. If the suction force applied to the soft tissue through an opening of the drainage tube exceeds capillary pressure, lymph is sucked out of the capillaries, resulting in suction injury. A normal capillary blood pressure is 40 torr. The vacuum pressure of the body cavity remains lower than the applied vacuum pressure to the drainage tube until all gas/fluid of the body cavity is removed and the soft tissue comes in direct contact with suctioning holes. At this state of equilibrium, if the suction force on the soft tissue exceeds the capillary blood pressure, suction injury occurs. Therefore, the safety of the drainage is inversely proportional to the suction force per opening area of a side hole or opening area of a hole at the end of the tube, whichever larger. It will be appreciated that a very small opening of 1 $mm^2$ can exert a suction force that reaches a capillary blood pressure only if an extremely high vacuum pressure of 4,000 torr is applied to the drainage tube. If the opening is a circular hole with a diameter of 1 mm (an opening area=0.785 $mm^2$), the critical vacuum pressure is 5,095 torr which is considerably higher than the vacuum pressure of current practice, around 10-15 torr. An addition safety feature of a tiny side hole is that a soft tissue, such as a coronary artery bypass vein graft, cannot be sucked into the side hole, which might cause kinking of the graft.

The efficiency of draining body fluids or blood is influenced by additional factors such as flow rate and transit time. For removing fresh blood, a transit time through the tube is a critical factor because blood must be removed out of the drainage tube before it clots. Flow rate of fluid/blood is proportional to the vacuum pressure and the fourth power of internal radius of the drainage tube. Transit time is proportional to internal lumen of the drainage tube divided by flow rate.

The present invention advantageously avoids injury risks, while achieving improved gas and fluid drainage efficiency through application of very high vacuum pressure. Existing chest drainage systems use a conventional vacuum pressure of 14.7 torr. Presently, vacuum pressure in and around the range of 25-35 torr is considered to be "high suction pressure." See U.S. Pat. No. 6,299,593 B1. Advantageously, and by sharp contrast, the present invention may use much higher vacuum pressures, preferably in the range of 50-500 torr or even more.

Currently, most, if not all, major medical facilities have a centralized vacuum source. The vacuum pressure from such source is typically regulated by a vacuum gauge mounted on a wall. A disposable plastic canister for fluid collection is also installed. Normally the vacuum pressure is adjusted by a wall-mounted gauge in a range of 0 to 500 torr. A similar range of vacuum pressure or even substantially higher vacuum pressure can be readily generated by existing battery-powered DC motor-vacuum pumps.

A small bore drainage tube for high vacuum pressure suction may be made of polymer such as polyurethane, silicone rubber or other biocompatible flexible polymer. The drainage tube may derive support and vacuum distribution benefit from a coaxial double-lumen structure, see U.S. Pat. No. 6,299,593 B1, or may be a single-lumen structure with a plurality of small side holes. Flow rate of fluid is proportional to the fourth power of the radius of the tube. A very high vacuum pressure compensates for the reduction of flow rate by small caliber tube. The small caliber tube provides easier, less painful insertion and removal.

FIG. 1A illustrates a perspective view of a drainage tube 101 in accordance with one embodiment of the present invention. The drainage tube 101 includes a first portion 102 without side holes, and a second portion 103 with side holes. One end is closed with an end plug 104 and the other end 106 is coupled to a connector 105 having a one-way check valve 107. The free end 108 of the connector 105 is adapted to be connected to a vacuum source.

FIG. 1B illustrates an enlarged, axial cross-sectional view near the tip of the drainage tube 101. The drainage tube 101 has a central bore 110. The wall of the drainage tube 101 is perforated to include small side holes 111 which communicate vacuum pressure from the central bore 110 to matter outside the drainage tube 101. The side holes 111 need not be circular. The end plug 104 prevents communication of vacuum pressure from the central bore 110 through the tip of the drainage tube 101.

FIG. 1C illustrates an enlarged perspective view of the connector 105. The connector 105 includes a one-way valve 107. A first end 109 of the connector 105 is configured to be connected to an end of the drainage tube 101, and the other end 108 of the connector 105 is configured to be connected to a vacuum source via a standard connecting tube. The one-way valve 107 may be a diaphragm type valve or another type of one-way valve.

FIG. 2 illustrates a representation of a vacuum chamber in accordance with an embodiment of the present invention. The vacuum chamber 201 is interposed between a drainage tube 101 and a vacuum source. The vacuum chamber 201 has an inlet port 202, a gas outlet port 206, and a fluid drainage outlet port 203. It will be appreciated that the vacuum chamber 201 may have more than one inlet port 202, and may, for example, have two or three inlet ports. The gas outlet port 206 is configured to be connected to a vacuum source via a standard connecting tube. The fluid drainage outlet port 203 may be configured to be connected to a fluid collection bag such as, for example, a standard blood collection bag (with or without anticoagulants), or a rigid fluid collection reservoir (see U.S. Pat. No. 6,352,525 B1).

The vacuum chamber 201 may have baffles 205 to separate gas and fluid. Fluid is drained by gravity through the fluid drainage outlet port 203, while gas is removed through the gas outlet port 206. A vacuum relief valve 204 may be installed in a wall of the vacuum chamber 201. The vacuum relief valve 204 regulates the level of maximal vacuum pressure inside the vacuum chamber 201 (and thus of a central bore of a drainage tube connected to the vacuum chamber) at a predetermined level.

In one embodiment, the vacuum relief valve is a spring-loaded type (see U.S. Pat. No. 6,352,525 B1), but may be another type of vacuum relief valve such as, for example, a diaphragm type similar to the one-way valve used with the connector 105.

The gas outlet port 206 of the vacuum chamber 201 is adapted to be connected to a source of vacuum pressure, preferably in the range of 50-500 torr, although pressures both lower and higher could be used. For drainage of viscous materials such as, for example, pus from an abscess may require substantially higher suction force which can be generated by much higher vacuum pressure, e.g., 2,000 torr. A standard central vacuum line that is currently available at the majority of medical facilities cannot reach such a high vacuum pressure, but a portable vacuum pump can. At this extremely high vacuum pressure of 2,000 torr, suction force through a circular side hole with a diameter of 1 mm is 0.2 N, which still remains at only 20% of the suction force generated by a conventional 28 F chest tube at a conventional vacuum pressure of 14.7 torr.

The vacuum relief valve 204 of the vacuum chamber 201 advantageously provides protection against unexpected and potentially dangerous applications of vacuum pressure in excess of the range that may be safely applied to the small caliber tube. In particular, in one embodiment, the vacuum relief valve 204 may open at a predetermined vacuum pressure threshold. The predetermined vacuum pressure threshold will depend on the characteristics of the drainage tube 101, but, generally, will be set at a level designed to minimize the risk of injury that could be caused by the suction force presented at any hole in the drainage tube. When the vacuum relief valve 204 opens due to presence of vacuum pressure exceeding the predetermined vacuum pressure threshold, the valve then directs substantial vacuum pressure force to dissipate with influx of atmospheric air into the vacuum chamber 201, equalizing the threshold. The vacuum relief valve 204 ensures that unsafe suction force will not be applied to body tissue in the cavity being drained.

The one-way valve of the connector 105 also advantageously provides protection against accidental disconnection of the drainage tube 101 from the vacuum source, which can result in the complication of atmospheric air being sucked into the body cavity. It will be readily appreciated that a one-way valve may be used to maintain vacuum pressure in one direction into a vacuum conduit. Thus, the drainage tube 101 with the one-way valve 107 can be used alone as a passive gas removing device, particularly when the degree of gas leak from the lung is minimal.

Side holes 111 in the drainage tube 101 will increase the total suction area of the drainage tube 101. The number of side holes 111 in the drainage tube 101 may be constrained by the circumference of the drainage tube 101. In one configuration, side holes 111 are created around the drainage tube 101. The distribution of side holes 111 along the tube 101 may be at a constant interval or progressively increasing interval or in any combination. The number and size of side holes 111 may be selected to maximize the total suction area without compromising the mechanical strength of the tube 101.

For a 12 F tube as an example, four side holes 111 of diameter of 1 mm ($1 \times 10^{-3}$ m) may be created per circumference and along 15 cm tube, 65 holes per line can be made without losing structural strength. Thus a total number of side holes 111 is 260 and total suction area is $2.041 \times 10^{-4}$ m$^2$. If the diameter of each side hole 111 is reduced to 50% (0.5 mm), 1,040 side holes 111 can be created. The total suction area is, however, the same, $2.041 \times 10^{-4}$ m$^2$, in either of these exemplary drainage tubes 101, and thus the total suction pressure is identical.

If vacuum pressure of 100 torr is applied to a side hole of 1 mm in diameter, the suction force through the opening is $7.85 \times 10^{-5}$ torr·m$^2$ ($100 \times \pi \times 0.0005^2$) or $1.0466 \times 10^{-2}$ N (N will be understood to mean Newtons). If the diameter of the side hole 111 is reduced to half, 0.5 mm, the suction force through the opening decreases to $1.96 \times 10^{-5}$ torr·m$^2$ or $2.616 \times 10^{-3}$ N. This means that the drainage tube 101 with a side hole 111 of 0.5 mm in diameter is four times safer than the drainage tube 101 with a side hole 111 of 1 mm in diameter at the same vacuum pressure applied to the drainage tube.

When a vacuum pressure is applied to one end of the drainage tube 101 and the other end is inserted into a body cavity containing fluid, the flow rate of the drained fluid through the drainage tube 101 is proportional to the vacuum pressure and the fourth power of the internal radius. A typical size of a conventional drainage tube for drainage of blood from the mediastinum following open heart surgery is 36 F and its internal diameter is about 8 mm. If the vacuum pressure is increased from the conventional 14.7 to 500 torr, the internal radius of the drainage tube can be reduced from 4 mm to 1.6563 mm ($14.7 \times 4^4 = 500 \, R^4$), while maintaining the same flow rate. If the wall thickness of the drainage tube is 0.5 mm, the size of this tube is 13 F. A 13 F tube can be inserted into a chest cavity through a needle puncture using an existing percutaneous insertion kit. The outer diameter of a 13 F tube is significantly smaller than that of a 36 F tube, and thus causes less pain at the site of skin penetration. The space taken up by one 36 F tube is equivalent to 7.7 of 13 F tubes. Therefore, another 13 F drainage tube can be added to double the flow rate without compromising the space inside the chest cavity. Because of the very small puncture hole required for insertion, the incidence of wound infection is lower than that associated with the surgical incision required for insertion of a conventional larger tube.

The present invention may operate with a vacuum chamber as described in U.S. Pat. No. 6,352,525 B1. It will be appreciated that additional inlet ports may be added, for example, two additional inlet ports. So configured, the vacuum chamber may accept up to three drainage tubes 101. A vacuum relief valve of the vacuum chamber may be a spring-loaded type as described in U.S. Pat. No. 6,352,525 B1, or a diaphragm type as illustrated in FIG. 2 or any other type that opens at the preset threshold to allow influx of atmospheric air to maintain the vacuum pressure of the vacuum chamber at the predetermined level. A rigid fluid collection reservoir, such as that described in U.S. Pat. No. 6,352,525 B1, may be replaced with a standard blood collecting plastic bag. A battery-powered vacuum pump may be detached and the gas outlet of the vacuum chamber may be directly connected to a central vacuum line of a medical facility, or other vacuum source external to the vacuum chamber.

In using a conventional chest drainage system, a conventional chest tube is inserted into the chest cavity through a surgically created incision and path. By contrast, a small bore drainage tube in accordance with the present invention is inserted into the body cavity using a percutaneous technique. First, for chest drainage, a needle punctures the chest wall and a guidewire is threaded through it. A small plastic sheath, e.g. 7 F, is inserted into the chest cavity over the guidewire. After the guidewire is removed, a 7 F drainage tube 101 is inserted into the chest cavity through the sheath. Then the plastic sheath is split while it is withdrawn from the body cavity, thus leaving the small bore drainage tube 101 in place. With the small bore drainage tube 101 in place, the output end of the connector 105 is connected to a vacuum chamber 201 using a standard connector tubing. In one application, a central vacuum source of a medical facility, typically capable of applying maximum of around 500 torr vacuum pressure, is connected to the gas outlet port 206 of the vacuum chamber 201. Such a central vacuum source includes a vacuum pressure gauge that allows a user to restrict the maximum vacuum pressure and to select a particular vacuum pressure. When gradual increase of vacuum pressure of the vacuum chamber 201 is desired, for example, to let a collapsed lung re-expand slowly in the treatment of spontaneous pneumothorax, the vacuum pressure is gradually increased over a 15 to 30 minute period.

Due to its high efficiency operating at high vacuum pressure, the present invention may advantageously reduce the incidence of subcutaneous emphysema (collection of air under the skin), unresolved pneumothorax, pleural effusion or cardiac tamponade. Because only a few sizes of the drainage tubes can take care of all indications, from air removal to blood evacuation after open heart surgery, inventory costs may advantageously be markedly reduced. Also a battery-powered portable vacuum pump allows for safer, more economical ambulatory care of medically stable patients with drainage tubes. The ambulatory care of these patients not only reduces medical costs but also avoids highly fatal hospital-acquired infections.

The present invention may be embodied in other specific forms without departing from the essential characteristics as described herein. The embodiments described above are to be considered in all respects as illustrative only and not restrictive in any manner. The scope of the invention is indicated by the following claims rather than by the foregoing description. Any and all changes which come within the meaning and range of equivalency of the claims are to be considered within their scope.

What is claimed is:

1. A drainage system for draining a body cavity, comprising:
    a source of vacuum being at a level of at least 300 mm Hg; and
    a tube having a first and a second end, said first end adapted to be inserted into the body cavity and being effectively closed, and a tube wall,
    a plurality of holes formed into said tube wall in an area of said tube that is intended to be inserted into the body cavity,
    a second end of said tube being adapted for connecting to said source of vacuum,
        said holes being of a size and quantity such that a suction force from any of said holes is insufficient to cause any significant injury to body tissue proximate a hole, while efficiently draining fluid from body cavity,
        wherein said tube is of a small caliber, and wherein a largest hole is approximately circular in diameter with an effective diameter no greater than about one half of an internal diameter of said tube in the region of said holes, and wherein said effective diameter is between about 0.5 mm and about 1 mm.

2. The drainage system of claim 1 wherein said hole size and vacuum level yield a force of about 0.4N at a hole.

3. The drainage system of claim 1, wherein an outer diameter of the tube is in the range of 4 F to 15 F.

4. The drainage system of claim 1, wherein an outer diameter of the tube is about 13 F.

5. The drainage system of claim 1 wherein said hole size and vacuum level yield a force in the range of about 0.2N to 0.8N at a hole.

* * * * *